United States Patent
Intelisano

(10) Patent No.: US 10,094,747 B2
(45) Date of Patent: Oct. 9, 2018

(54) PASSIVE DIFFUSION SAMPLER

(71) Applicant: Summit Holding Company, LLC, Cheyenne, WY (US)

(72) Inventor: Craig Intelisano, Bradenton, FL (US)

(73) Assignee: Summit Holding Company, LLC, Cheyenne, WY (US)

( * ) Notice: Subject to any disclaimer, the term of this patent is extended or adjusted under 35 U.S.C. 154(b) by 318 days.

(21) Appl. No.: 14/887,841

(22) Filed: Oct. 20, 2015

(65) Prior Publication Data

US 2016/0041073 A1  Feb. 11, 2016

Related U.S. Application Data

(62) Division of application No. 13/478,703, filed on May 23, 2012, now Pat. No. 9,194,771.

(60) Provisional application No. 61/457,737, filed on May 23, 2011.

(51) Int. Cl.
*G01N 1/10* (2006.01)
*G01N 1/22* (2006.01)

(52) U.S. Cl.
CPC .............. *G01N 1/22* (2013.01); *G01N 1/10* (2013.01)

(58) Field of Classification Search
CPC .... G01N 2001/4016; G01N 1/10; G01N 1/22; E21B 49/08; E21B 49/081
USPC ...................................... 73/863.23
See application file for complete search history.

(56) References Cited

U.S. PATENT DOCUMENTS

| | | |
|---|---|---|
| 3,640,393 A | 2/1972 | Hurtig |
| 5,804,743 A | 9/1998 | Vroblesky |
| 5,996,423 A | 12/1999 | Baghel |
| 6,148,914 A * | 11/2000 | Guieze ................ E21B 36/04 166/163 |
| 6,244,117 B1 | 6/2001 | Mengel |
| 9,194,771 B2 * | 11/2015 | Intelisano .............. G01N 1/22 |
| 2007/0269350 A1 | 11/2007 | Coyne |
| 2008/0314844 A1 | 12/2008 | Intelisano |
| 2014/0290391 A1 | 10/2014 | Varhol |

FOREIGN PATENT DOCUMENTS

SU         345269 A  *  4/1968

OTHER PUBLICATIONS

Final Office Action for U.S. Appl. No. 13/478,703 dated Feb. 26, 2015.

(Continued)

*Primary Examiner* — Helen Kwok
*Assistant Examiner* — Nashmiya Fayyaz
(74) *Attorney, Agent, or Firm* — Butzel Long; Gunther J. Evanina

(57) ABSTRACT

A passive diffusion sampler and kit that includes a passive diffusion sample bag comprising a regenerated cellulose membrane to allow for sampling of a broad spectrum of contaminants and VOCs. The sample bag is disposed in a rigid housing which protects the bag from tearing and also allows the housing to be inverted to suspend the bag upside down and provide a user access to a fluid outlet means on the bag for withdrawing a sample from the bag without agitating the sample.

9 Claims, 2 Drawing Sheets

(56) References Cited

OTHER PUBLICATIONS

Non Final Office Action for U.S. Appl. No. 13/478,703 dated Nov. 7, 2014.
Notice of Allowance and Fee(s) Due for U.S. Appl. No. 13/478,703 dated Jul. 17, 2015.
Entire patent prosecution history of U.S. Appl. No. 13/478,703, filed May 23, 2012, entitled, "Passive Diffusion Sampler".

* cited by examiner

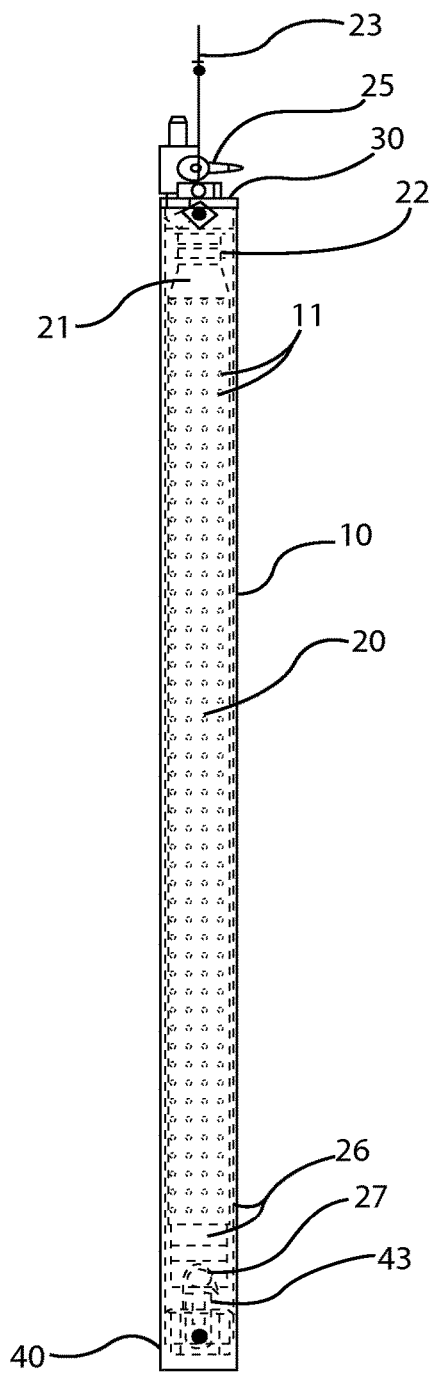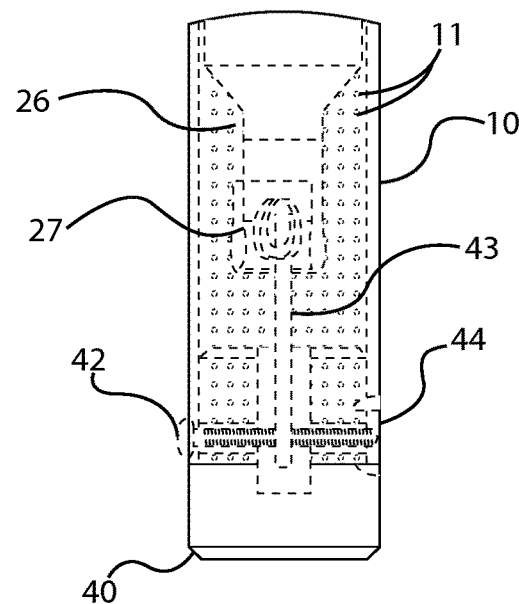
FIG. 2
FIG. 3

PASSIVE DIFFUSION SAMPLER

CROSS REFERENCE TO RELATED APPLICATIONS

This application is a divisional of U.S. Non-Provisional patent application Ser. No. 13/478,703, filed May 23, 2012, which claims priority to U.S. Provisional Patent Application No. 61/457,737, entitled "PASSIVE DIFFUSION SAMPLER," filed on May 23, 2011, the contents of which are incorporated herein by reference in their entirety.

FIELD OF THE INVENTION

The present invention relates to passive diffusion samplers. More particularly, the present invention relates to an improved passive diffusion samplers and kits comprising a regenerated cellulose diffusion bag for capturing a broad spectrum of ground water contaminants and optionally a rigid perforated housing for protecting the diffusion bag and/or a piercable septa assembly for removing samples without the risk of air contamination in the process, or alternatively, a flow control valve for safely removing larger samples.

BACKGROUND OF THE INVENTION

Passive diffusion samplers are known in the art. As background, U.S. Pat. No. 5,804,743 to Vroblesky et al., which is hereby incorporated by reference in its entirety, provides a thorough discussion of passive diffusion sampling and describes one commonly used sampler arrangement.

As will be appreciated, typically, prior art passive diffusion samplers work by submersing a tubular low density polyethylene bag filled with analyte-free water into a ground water sampling bore hole. The polyethylene bag serves as a semi-permeable membrane that allows certain VOCs to diffuse through the membrane. Over time, an equilibrium is established between the VOCs in the bag and those in the groundwater. The sample bag is retrieved from the sample well after reaching equilibrium (typically after a two-week deployment) and the bags are opened and specimen vials are filled and sent to the laboratory for quantitative analysis. As will be appreciated by those of ordinary skill in the art, one major drawback with polyethylene bags is the inability of certain water contaminants, such as certain VOCs including certain ketones, ethers, and alcohols, to penetrate the membrane and be accounted for in the specimen samples sent to the laboratory.

Another known drawback of the Vroblesky et al. passive diffusion sampler described in the '743 patent involves the inherently fragile nature of polyethylene sample bags. Experience has shown that these bags were susceptible to tearing while being deployed or retrieved after deployment by snagging pointed edges of rocks and the like in the sample bores. The devastating loss of a sample bag after waiting two weeks for it to reach equilibrium is a significant problem in the art. Other prior artisans have suggested the use of a netting over the sampler to protect the bag from snags and tears. While this configuration has reduced the problem of snagging and tearing, there is still a long-felt, yet unresolved need in the art for a tear-free sampler.

The prior art suffers from yet another drawback that has been recognized by the present inventor. With the prior art samplers in use today, samples are collected by removing a bag cap and pouring them into sample vials. By design, these sample bags expose the water sample to the ambient air before the vial is sealed and sent for testing. The contamination of the sample by exposure to air is a problem the present inventor has recognized and solved through some embodiments of the present invention.

The foregoing underscores some of the problems with conventional passive diffusion samplers and bags. Furthermore, the foregoing highlights the long-felt, yet unresolved need in the art for a passive diffusion sampler that can sample for a broader universe of VOCs and contaminants in groundwater. Likewise, the foregoing highlights the long-felt, yet unresolved need in the art for a truly tear-free passive diffusion sampler system and bag. In addition, the foregoing highlights the inventor's recognition and need in the art for a passive diffusion sampler system capable of providing groundwater samples free from contamination by air.

SUMMARY OF THE INVENTION

Various embodiments of the present invention overcome various of the aforementioned and other disadvantages associated with prior art passive diffusion samplers and bags and offers new advantages as well. According to one aspect of various embodiments of the present invention there is provided a passive diffusion sampler having a sample bag adapted for sampling a greater universe of VOCs and other water contaminants. In a presently preferred embodiment, the passive diffusion sampler includes a sampler bag comprising regenerated cellulose. One advantageous feature of this embodiment of the invention is the ability for the regenerated cellulose to serve as a membrane permeable to all or almost all VOCs and other water contaminants of interest. In another presently preferred embodiment, the passive diffusion sampler comprises a kit for quick assembly and deployment in a groundwater sample well. In accordance with this aspect of the invention, the regenerated cellulose is stored and transported in a moist environment to prevent the bag from drying out and degrading.

According to another aspect of various embodiments of the present invention there is provided a passive diffusion sampler having a rigid, perforated housing for suspending therein a passive diffusion sampler bag and protecting the bag from snags and tears during deployment and retrieval into a groundwater sampling bore. In a presently preferred embodiment, the housing comprises a length of PVC tubing sized to accept a sampler bag and having a sidewall provided with a plurality of holes in a number and/or sized to allow the system to reach equilibrium after submersion in a groundwater sampling well. In a related presently preferred embodiment, the housing includes a top end cap configured to accept the top of a sampler bag and suspend the bag centrically in the housing away from and out of contact with the sidewalls of the PVC tubing.

In accordance with yet another aspect of various embodiments of the present invention, the passive diffusion sampler includes a bottom end cap at the bottom of the housing. In accordance with these embodiments of the invention, the passive diffusion sample bag is preferably configured to be attached or attachable to the bottom end cap, thereby allowing the bag to be suspended centrically in the tube but also allowing the bag to remain suspended from bottom end cap when the housing is inverted. In some embodiments, the bottom end cap may also be adapted to comprise or suspend a sink weight(s) therefrom via clips or the like to aid the complete submersion of the system into the groundwater to be sampled.

One advantageous feature of the embodiments of the invention including a bottom end cap is the ability to invert the system without the bag falling over. In accordance with a presently preferred embodiment, the sample bag may be equipped with a septa on the top of the bag. The septa of the bag allows a syringe needle or the like to inserted into the top of the bag so a sample can be withdrawn from bag without it being exposed to, and potentially contaminated by, air as is the case in prior art systems where a screw cap is removed and sample vials filled by pouring the contents of the bag. As will be appreciated by one of ordinary skill in the art armed with the present specification, embodiments of the present invention making use of a septa on the top of the bag are particularly aided by the ability to invert the housing and suspend the bag to provide easy access to the septa for withdrawing samples.

The invention as described and claimed herein should become evident to a person of ordinary skill in the art given the following enabling description and drawings. The aspects and features of the invention believed to be novel and other elements characteristic of the invention are set forth with particularity in the appended claims. The drawings are for illustration purposes only and are not drawn to scale unless otherwise indicated. The drawings are not intended to limit the scope of the invention. The following enabling disclosure is directed to one of ordinary skill in the art and presupposes that those aspects of the invention within the ability of the ordinarily skilled artisan are understood and appreciated.

BRIEF DESCRIPTION OF THE DRAWINGS

Various aspects and advantageous features of the present invention will become more apparent to those of ordinary skill when described in the detailed description of a preferred embodiment and reference to the accompany drawing wherein:

FIG. 2 depicts a cross-sectional view of an additional embodiment of a passive diffusion sampler kit according to the instant invention; and FIG. 3 depicts a cross-sectional view of the bottom portion of the passive diffusion sampler kit of FIG. 2.

DETAILED DESCRIPTION OF A PREFERRED EMBODIMENT

Figure 1:
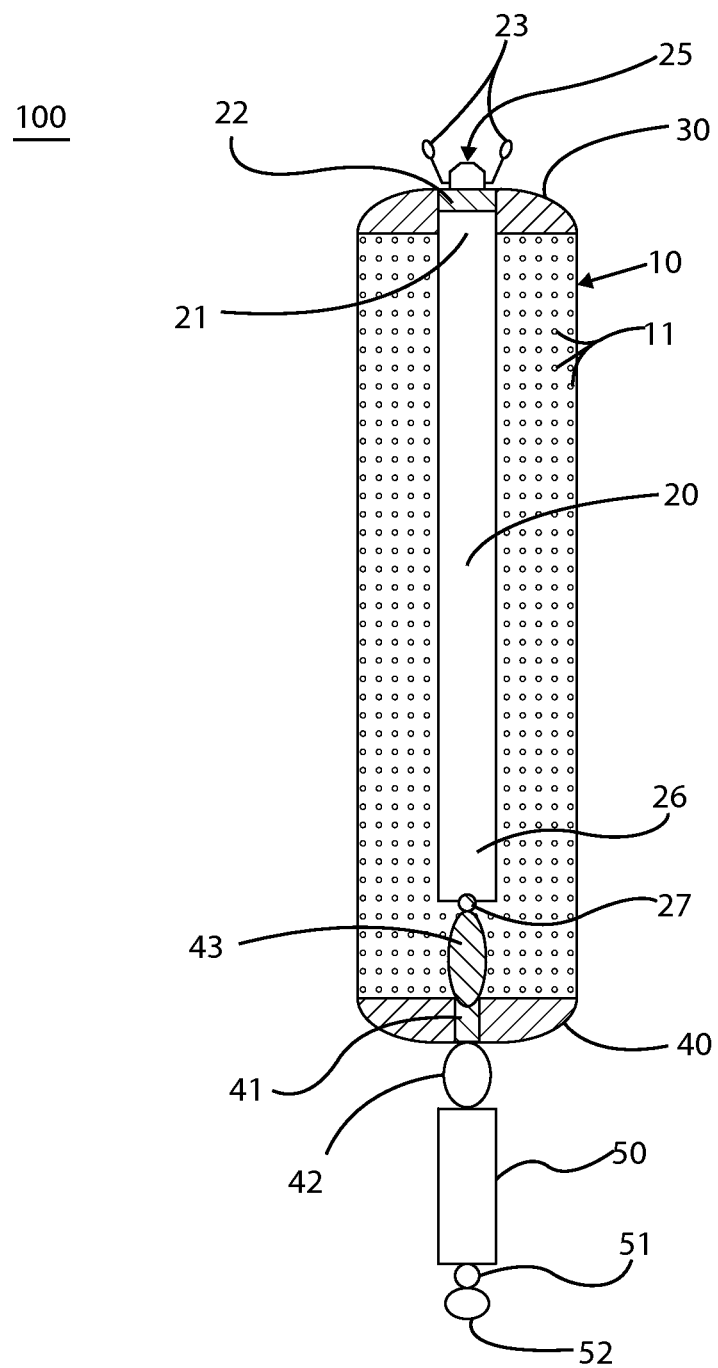
FIG. 1 depicts a cross-sectional view of an exemplary embodiment of a passive diffusion sampler kit assembled for deployment in accordance with the present invention.

A presently preferred embodiment of a passive diffusion sampler incorporating various advantageous features of various embodiments of the invention is depicted in FIG. 1. As shown, passive diffusion sampler 100 comprises a perforated housing 10 including a sidewall defining a plurality of perforations 11. The housing 10 may comprise any suitable material adapted for safe immersion in its intended environment, in this case, submersion in groundwater. "Suitable material" in connection with this description of the preferred embodiment is intended to convey that the housing is rigid enough to protect the sample bag from tears or snags, composed of a material that is environmentally and operationally safe for immersion in water, durable enough for repeated use, and has the added benefit of serving as a sink weight further reducing the size, cost, and expense of the system.

In a presently preferred embodiment, the housing 10 comprises a length of a rigid PVC tube or conduit having an interior sized to receive a sample bag, that upon filling, will remain clear of the sidewalls. The PVC is provided with perforations in a size, quantity, and/or configuration adapted to ensure it does not interfere with the ability of the sampler bag to reach equilibrium. Any other suitable material may be used instead of PVC tubing, but cost, availability and durability make PVC a presently preferred housing material.

Disposed within the housing is a passive diffusion sample bag 20. While the advantages of the present invention realized by the provision of a PVC or similar rigid housing translate to any suitable passive diffusion bag, a particularly advantageous feature of a presently preferred embodiment of the invention is realized from the provision of a sample bag comprising regenerated cellulose. According to this advantageous feature, any suitable regenerated cellulose may be used in connection with these embodiments of the present invention. Routine experimentation will allow one of ordinary skill in the art to determine the suitability and parameters for sample bags of any particular make, thickness, or type for use in a given environment with a given sampler.

As will now be appreciated, regenerated cellulose allows the passive diffusion sampler to equilibrate with virtually every contaminant properly and proportionally represented in the sample bag. Unlike polyethylene bags, which are known to be limited to specific VOCs to the exclusion of others, the regenerated cellulose bags of the present invention allow passive diffusion samplers to overcome these known disadvantages of passive diffusion sampling. While the present inventor is the first to employ regenerated cellulose membranes as the material for a passive diffusion sampler bag, those of ordinary skill in the art armed with the present specification will now be able to appreciate the advantages and superior sampling ability realizable through the use of regenerated cellulose membranes to overcome the disadvantages of polyethylene sample bags.

Returning to FIG. 1, the passive diffusion sample bag 20 has a top neck or opening 21 sealed by a bag cap 22. The bag cap 22 and top neck 21 can be of any suitable configuration that provides for a fluid tight seal. Typical arrangements include interlocking threads. Alternatively, the bag cap 22 can be partially sheathed into the sample bag 20, with the sample bag 20 held in place on the bag cap 22 by a collar (not shown). The cap 22 can be manufactured integral with the bag 20 or as a separate cooperating piece. In operation, the bag cap 22 is removed or opened to allow the bag to be filled with analyte-free water prior to insertion in a well bore and to allow the equilibrated water to be poured into sample vials after the bag is retrieved from the sample bore.

As also shown in FIG. 1, the neck 21 or cap 22 includes a suspension member 23, which in the depicted embodiment and common in the art, comprises a pair of lateral eye hook members adapted for receiving string or wire for securing the sampler 100 to allow it to be lowered and lifted in and out of the sample bore by a user from the surface.

In accordance with one advantageous feature of some embodiments of the invention, the sampler 100 depicted in FIG. 1 includes a sample outlet 25 comprising a piercable septa or alternatively (or even interchangeably), a flow control valve. A flow control valve as the sample outlet 25 is preferable in those embodiments where a large sample, e.g., 1-liter, is needed or the contents of the bag need to excised. The sample outlet is preferably configured to allow the sample to be withdrawn without agitating the contents of the bag. In a preferred embodiment, the flow control valve is configured to snap-on or otherwise fit with or in place of cap 22. A passive diffusion sampler kit according to the invention may also be provided with interchangeable sample outlets, wherein a septa or flow control valve can be alternatively snap, screwed, or otherwise connected to the bag for a given sampling.

According to certain preferred embodiments of the invention, the sample outlet comprises a septa 25. Preferably, the septa is disposed as or in the cap 22, but the exact position and configuration of the septa are not critical to realize the benefits of the its inclusion. All that is required is that the septa allow access to the contents of the bag 20, preferably without agitation of the sample. In operation, the present inventor envisions the septa being pierced by a syringe or needle to allow samples to be withdrawn from the bag 20 and deposited directly into sample vials without the sample being subjected to exposure or contamination with air (as is the case when contents are poured into vials).

To facilitate the use of the sample outlet 25, whether in the form of a septa or flow control valve, a presently preferred embodiment of the present invention makes use of one or more end caps 30, 40 for the housing 10. While the end caps 30, 40 provide other beneficial uses and advantages, they are particular advantageous in connection with the sample outlet septa and fluid control valve embodiments of the invention.

To be more particular, the top end cap 30 is preferably configured to accept a sample bag 20 disposed through a central opening. This disposition not only ensures that the bag 20 remains within, and thereby protected from tearing by, the rigid housing 10; but also allows the bag 20 to remain out of contact with the sidewalls of the housing 10 when deployed to allow for the natural flow of groundwater through the bag 20, as well as ensuring debris does not enter and become trapped in the housing 10.

While the bottom end cap 40 may, in some embodiments, ensure that debris does not enter the housing from below during deployment, it plays a more significant role in the septa 25 embodiments of the invention. As shown in FIG. 1, the bottom end cap 40 includes a central post 41 for securing a first clip member or retainer 42 that is adapted for receiving a sink weight 50. As will be appreciated, sink weights may be necessary to ensure the sampler is and remains fully submerged to a suitable depth in the water when deployed. The sink weight 50 in turn preferably includes a clip or connector 51 including an eye hook 52 for attaching a second weight (not shown) for those applications requiring additional weights to be used.

Turning briefly to FIG. 2, in a particularly preferred embodiment, the bottom end cap 40 itself is manufactured of suitably dense and heavy material in order to serve as a sink weight. In this manner, the need for external sink weights (i.e., sink weights attached to the bottom end cap 40 as shown in FIG. 1) may be obviated. As shown in FIG. 3, the bottom end cap 40 may be secured to housing 10 by way of a screw 42 and nut 44. Upon reading the disclosure contained herein, additional ways to secure the bottom end cap 40 to housing 10 will become apparent to one of ordinary skill in the art including, e.g., providing threads on the bottom end cap 40 and the inside of housing 10 to allow threadable mating. Moreover, additional sink weights (not shown) could be attached to the bottom end cap 40.

Returning to FIG. 1, the bottom end cap 40 also preferably includes a bag clip 43 attached to the central post 41. The bag clip 43 in turn is connected to the bottom of the sample bag 26 by threading through an eye hole 27 provided integral with the bottom of the sample bag 26. Alternatively, the bag clip 43 could simply have a friction hold on the bottom of the bag. Other alternative means for holding the bag are suitable for purposes of the present invention and a laundry list of such methods and techniques is beyond the scope and purpose of this specification. Suffice it to say that any suitable method of holding the bag to the bottom of the sampler 100 should be understood as falling within the scope of the invention.

Returning to FIG. 1, the ability to secure the bottom of the bag 26 to the bottom cap 40 provides the advantageous feature of allowing the sampler to be inverted without the bag 20 falling over. In other words, the bag remains gravitationally suspended in a tubular form with any air in the bag now rising upwards towards the bag bottom 46 and away from the sample outlet 25. Once inverted, the sample outlet 25 allows a sample to be removed without agitating the bag contents and/or exposing the sample to ambient air. In one embodiment, the sample outlet includes a septa such that a syringe or needle can pierce the sample outlet septa 25 and remove a liquid sample. In an alternate embodiment, the sample outlet septa 25 is removable by unscrewing or the like, so that a sample outlet flow control valve 25 attachment can be used instead.

In this regard, the rigid housing 10, hereintofore unheard of with passive diffusion samplers, includes the added advantage of allowing the system to be inverted and free standing. While the depicted embodiment is shown utilizing a central post, clips, eye hole in the bag, and other specific mechanical structures, one of ordinary skill in the art armed with the present specification will readily appreciate that the advantageous features and aspects of the invention realized by this configuration is easily adapted to other configurations and structures that allow for the functions of holding and suspending the various components to allow for the use of the sampler 100 as describe herein to be achieved.

The above embodiments are for illustrative purposes and are not intended to limit the scope of the invention or the adaptation of the features described herein to particular types of passive diffusion samplers. Those skilled in the art will also appreciate that various adaptations and modifications of the above-described preferred embodiments can be configured without departing from the scope and spirit of the invention. Therefore, it is to be understood that, within the scope of the appended claims, the invention may be practiced other than as specifically described.

What is claimed is:

1. A passive diffusion sampler kit comprising:
    a sample bag comprising regenerate cellulose stored in a moistened enclosure until needed for sampling, the bag removable from the enclosure for filling with analyte-free water before deployment in a sample well,
    a rigid housing configured for accepting the sample bag, and
    retaining means for releasably holding the sample bag to a top end and bottom end of the housing but out of contact with the housing, thereby allowing the sample bag to be inverted.

2. The passive diffusion sampler kit of claim 1, further comprising:
    a syringe for piercing a septa disposed on the sample bag, wherein when the sample bag is inverted the syringe is inserted into the septa to remove a sample from the sample bag without exposing or contaminating the sample with ambient air.

3. The passive diffusion sampler kit of claim 1, further comprising:
    a control valve disposed on the sample bag, wherein when the sample bag is inverted the flow control valve is actuated to remove a sample from the sample bag without agitating the sample.

4. The kit of claim 1, further comprising:
a pair of outlet members comprising a first outlet member comprising a septa and a second outlet member comprising a flow control valve, wherein one of the first and second outlet members is used to withdraw a sample from the sample bag.

5. The kit of claim 4, wherein the first and second outlet members are interchangeable.

6. The kit of claim 4, wherein the first outlet member is removable and replaceable with the second outlet member.

7. The kit of claim 4 wherein the second outlet member is removable and replaceable with the first outlet member.

8. The kit of claim 4, further comprising a weight system for attachment to the bottom end of the housing.

9. The kit of claim 4, wherein the bottom end of the housing comprises a weight system.

* * * * *